(12) United States Patent
Davis et al.

(10) Patent No.: US 6,593,513 B2
(45) Date of Patent: Jul. 15, 2003

(54) ENDOGLUCANASE GENE PROMOTER UPREGULATED BY THE ROOT-KNOT NEMATODE

(75) Inventors: Eric L. Davis, Raleigh, NC (US); Melissa Goellner, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 09/772,219

(22) Filed: Jan. 29, 2001

(65) Prior Publication Data

US 2002/0019999 A1 Feb. 14, 2002

Related U.S. Application Data

(60) Provisional application No. 60/178,883, filed on Jan. 28, 2000.

(51) Int. Cl.[7] .............. C12N 15/09; C12N 15/29; C12N 15/82; C12N 15/10; A01H 5/00
(52) U.S. Cl. ................ 800/279; 800/278; 800/287; 800/298; 800/317; 800/320; 800/302; 800/306; 435/419; 435/418; 435/468
(58) Field of Search .................. 800/278, 279, 800/287, 298, 302, 320, 317, 306; 435/419, 468, 418

(56) References Cited

U.S. PATENT DOCUMENTS

| | | | |
|---|---|---|---|
| 5,530,187 A | * 6/1996 | Lamb et al. ............... | 800/205 |
| 5,589,622 A | 12/1996 | Gurr et al. | |
| 5,750,386 A | 5/1998 | Conkling et al. | |
| 5,770,786 A | * 6/1998 | Sijmons ...................... | 800/200 |
| 6,005,092 A | 12/1999 | Shoseyov et al. | |
| 6,228,643 B1 | * 5/2001 | Greenland et al. .......... | 435/419 |
| 6,433,252 B1 | * 8/2002 | Kriz et al. .................. | 800/287 |
| 6,437,217 B1 | * 8/2002 | McElroy et al. ............ | 800/278 |
| 6,437,221 B1 | * 8/2002 | Kunz .......................... | 800/287 |

FOREIGN PATENT DOCUMENTS

WO     WO92/21757     * 12/1992

OTHER PUBLICATIONS

Kim et al, "A 20 nucleotide upstream element is essential for the nopaline synthase (nos) promoter activity", 1994, Plant Molecular Biology vol. 24 pp. 105–117.*

Zane et al, "Cloning and characterization of elongation specific endo–1,4–B–glucanase (cel1) from *Arabidopsis thaliana*", 1997, Plant Molecular Biology, vol. 34, pp. 837–842.*

Shani, Ziv, et al., *Cloning and characterization of elongation specific endo–1,4–β–glucanase (cel1) from Arabidopsis thaliana, Plant Molecular Biology*, vol. 34, pp. 837–842 (1997).

* cited by examiner

*Primary Examiner*—Elizabeth F. McElwain
*Assistant Examiner*—Medina A. Ibrahim
(74) *Attorney, Agent, or Firm*—Myers Bigel Sibley & Sajovec

(57) ABSTRACT

The present invention provides a DNA construct comprising a root knot nematode responsive promoter, preferably the Arabidopsis cel1 promoter or promoters that hybridize thereto, operatively associated with a heterologous DNA segment that encodes a product disruptive of nematode attack. Plants and plant cells using the same and methods of use thereof are also disclosed.

8 Claims, 1 Drawing Sheet

SEQUENCE LISTING

```
<160> NUMBER OF SEQ ID NOS: 1

<210> SEQ ID NO 1
<211> LENGTH: 1614
<212> TYPE: DNA
<213> ORGANISM: Arabidopsis thaliana

<400> SEQUENCE: 1
```

-continued

```
acctgcaggt caacggatca catgcatcag cactatttac aacaatcctt tagggtatat      60
gttagtcaac cccgtaacac cattcgtacc cattaatcat gaacatttcg caaagttttc     120
ccaccaaaaa cggcgtcgga taaggttttt ggcattttgt gtttcttttt ttgtgtgcat     180
agcataattt cattttaacc gtactattcg aagattttta aattggataa agatgattca     240
ttcattacat agtcgctttg ttgttactag tgataaattc atgttaatga ttctatgatt     300
ttcggccagc tatctcatta attattaaga cgtttaagtg gagctattag caatcgtgta     360
tgacataatg attagcattt tcatgtgcca tgcccatgca tgaggctttt ttttgtttaa     420
aattttattc tattatatcc gaattttgtt atatactaaa tgaacatttg tctctgattt     480
ggtctactag ttaattaacc tttagcttca ctaataaaaa atctcatgat tttgatactt     540
aaacccaaaa catattaaaa acaattagca gtcttttaaa tcgataatgt gcttagatga     600
ttatacgttc gtaggaaact cttttgtttc caatgcatgt taagaactaa gaactcgtat     660
ccttaagcac caatgcttta tgcttaatgc ctcattagag atataaactg agattgactg     720
tgttctgaat catcataata taaggcacac aaagaacaga acaggaaata cttagcaata     780
taataggttt ccaataaaag tgaagaagaa tacaataaac ttttataaaa aaaaaagtat     840
ataataattt cacactcgaa tcaaccaaat gtaagatgtc ttgtccattt acacatcaca     900
tgagtaagtg gattacagat tgcaattgat gaaatctgga tcttagctaa aaatttatta     960
cgttactata tacatcgagt tttaagatgt tcataatcac aaccacaacc acaagtttga    1020
agaaataaga aacagagtaa taatatatca aataaaattt catggctgat ggaatctttt    1080
ttctaattgt aggtccaaaa aagcctaaat taatggggaa acaaaaacca aaattcaata    1140
gtaattttac taattatgtc ttggttaaat agagtaaaaa gaaaattaat cacaaacctc    1200
caaaaatcaa ctaattgaga tcaaaacacg tgtcgcatgc caatagggcg gtggatcaca    1260
tggtaaaaaa attcacttta attttgtct ttcttcataa ttcatctcac agatttcaac    1320
ttctcttttg gattctctca ccgtacaccg tcggcgtacc actcccctc cacaccgtcg    1380
gtattaaaaa tctcaaaccc taaaaccgt atccaataac ccacccggtc caaccggtta    1440
ttcaaacccg gtcaatccaa aattcgcctc ggaatccaaa cctccatacc caatctaaca    1500
tggaaaaacc tccaatcaca aacctccacg tggtgatcac tcattggctc ttattctgga    1560
atccaagagg accttttttag tataaagagc cccttcgttg gtcctatcac cttc         1614
```

ENDOGLUCANASE GENE PROMOTER UPREGULATED BY THE ROOT-KNOT NEMATODE

RELATED APPLICATIONS

This application claims the benefit of U.S. provisional application Ser. No. 60/178,883, filed Jan. 28, 2000, the disclosure of which is incorporated by reference herein in its entirety.

FIELD OF THE INVENTION

This invention relates to tissue-specific gene promoters, and particularly relates to a promoter which is responsive to the root knot nematode.

BACKGROUND OF THE INVENTION

A promoter is a DNA sequence which flanks a transcribed gene, and to which RNA polymerase must bind if it is to transcribe the flanking gene into messenger RNA. A promoter may consist of a number of different regulatory elements which affect a structural gene operationally associated with the promoter in different ways. For example, a regulatory gene may enhance or repress expression of an associated structural gene, subject that gene to developmental regulation, or contribute to the tissue-specific regulation of that gene. Modifications to promoters can make possible optional patterns of gene expression, using recombinant DNA procedures. See, e.g., Old and Primrose, Principles of Gene Manipulation (4th Ed., 1989).

U.S. Pat. No. 5,459,252 to Conkling and Yamamoto describes a root specific promoter designated RB7, which was identified in tobacco. U.S. Pat. No. 5,837,876 to Conkling et al. describes a root cortex specific gene promoter designated the RD2 promoter, which was also identified in tobacco.

Rather than use a promoter that is constitutively active, it is desireable to have promoters that are responsive to particular stimuli. In particular, if a promoter is responsive to a particular pathogen, then that promoter could be used to impart selective disease resistance to that pathogen through expression of a transgene that disrupts that pathogen.

U.S. Pat. No. 5,750,386 to Conkling, Opperman and Taylor describes pathogen resistant transgenic plants in which a nematode-responsive element is operatively associated with a nucleotide of interest (in this case, a gene encoding a product toxic to plant cells). One nematode responsive element was a deletion fragment of the RB7 root specific promoter described above.

U.S. Pat. No. 5,589,622 to Gurr et al. suggests nematode resistant transgenic plants in which cells of the plant contain a heterologous construct comprising a nematode responsive promoter operatively associated with a product disruptive of nematode attack. However, the DNAs disclosed by Gurr et al. as nematode responsive promoters do not appear to represent such promoters, and instead appear to represent extraneous or irrelevant DNA.

To impart useful traits to plants by the expression of foreign genes using genetic engineering techniques, a variety of pathogen-responsive promoters will be required to allow traits to be expressed selectively, in the appropriate plant tissues, and at the appropriate times. Accordingly, there is a continued need for pathogen responsive elements that operate in plant cells.

SUMMARY OF THE INVENTION

The present invention is based on the discovery that the elongation specific endo-1,4-β-glucanase (cel1) promoter of *Arabidopsis thaliana*, described in U.S. Pat. No. 6,005,092 to O. Shosoyev and Z. Shani (Dec. 21, 1999), and Shani et al., *Plant Molecular Biology* 34, 837–842 (1997), is upregulated in root-knot nematode feeding cells (i.e., giant cells). Plant parasitic nematodes cause approximately 100 billion dollars annually in crop loses worldwide. The root knot nematode has a host range of over 2000 plant species, and is one of the most damaging nematodes.

Accordingly, a first aspect of the present invention is an isolated DNA molecule which directs root knot nematode responsive transcription of a downstream heterologous DNA segment in a plant cell (i.e., a promoter), and the use thereof in providing or imparting nematode resistance to plants and plant cells.

A further aspect of the present invention is construct comprising a promoter as described above and a heterologous DNA segment (i.e., a DNA segment not naturally associated with that promoter) positioned downstream from, and operatively associated with, the promoter. The heterologous DNA segment preferably encodes a product disruptive of nematode attack (i.e., a product that hinders or interferes with the ability of a nematode to feed upon a plant cell, or establish a feeding site in relationship to a plant cell, when that product is expressed in a plant cell).

Further aspects of the present invention are plant cells containing the above described constructs, methods of making transformed plants from such plant cells, the transformed plants comprising such transformed plant cells, and the use of the foregoing to impart resistance to root knot nematodes to plants.

DETAILED DESCRIPTION OF PREFERRED EMBODIMENTS

Figure 1:
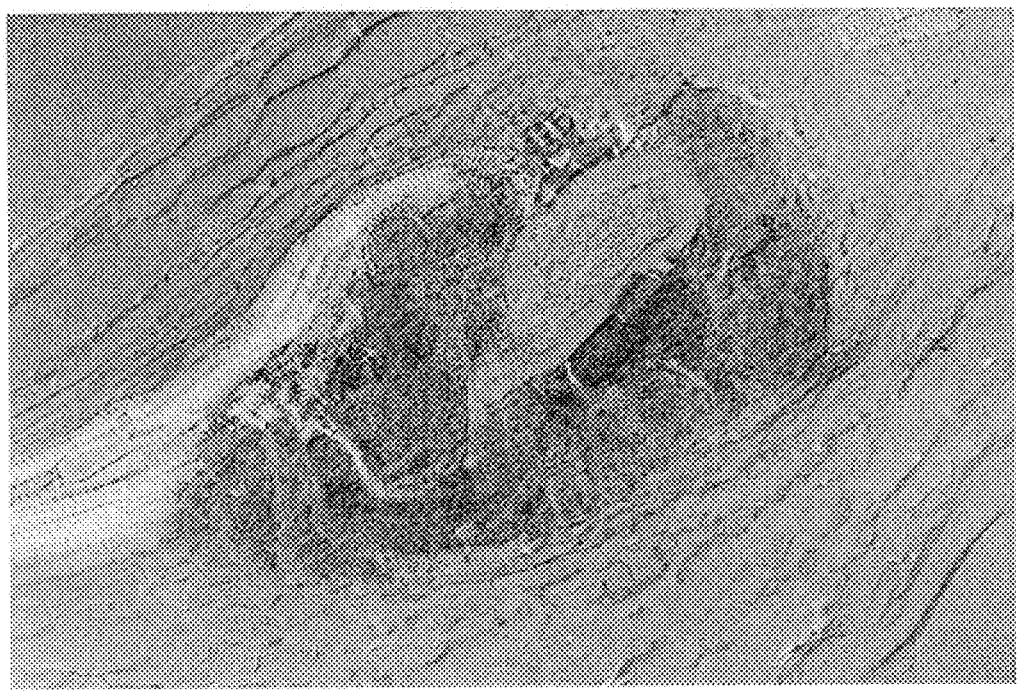
FIG. 1 illustrates the upregulation of cel1::GUS expression in root knot nematode (RKN)-induced giant cells in the root of tobacco plants.

Various preferred embodiments of the present invention are set forth below. These embodiments are not intended to provide a detailed catalog of all manner in which the instant invention may be carried out, as numerous variations will be apparent to persons skilled in the arts to which the invention pertains. Accordingly, the following is set forth for illustrative purposes, and is not intended to be limiting of the invention.

1. Root Knot Nematodes

The invention may be carried out to protect plants from root knot nematodes (Meloidogyne spp.). Root-knot nematodes are sedentary endoparasites with an extremely intimate and complex relationship to the host plant. The infective second stage juvenile (J2) is free in the soil. Upon location of a host root, the J2 penetrates the root intercellularly in the region just posterior to the root cap and migrates to the developing vascular cylinder. The nematode then orients itself parallel to the cylinder and injects glandular secretions into the plant cells surrounding its head, resulting in the initiation of nematode feeding cells. These 5–7 cells undergo rapid nuclear divisions, increase tremendously in size, and become filled with pores and cell wall invaginations. The feeding site cells, or "giant cells", function as super transfer cells to provide nourishment to the developing nematode. During this time, the nematode loses the ability to move and swells from the normal eel shaped J2 to a large, pear shaped adult female. As the nematode feeds on the giant cells, parthenogenic reproduction results in the disposition of 300–400 eggs. This entire process occurs over the span of 20–30 days, and root-knot nematodes may complete as many as 7 generations during a cropping season. Thus, in addition to delivering at the feeding site a product that is toxic to the nematode, it will be seen that, by causing the plant itself to kill or disable the cells upon which the pathogen must feed, the pathogen will be much less successful at infecting the plant.

2. Promoters

As used herein, a nematode responsive (or "nematode inducible") promoter refers to a promoter that (a) does not normally drive transcription in a plant cell except when that cell resides in tissue infected by a root knot nematode, or (b) normally drives transcription in a plant cell, and which drives increased levels of transcription when that cell resides in tissue infected by a root knot nematode. The promoter may be a naturally occurring promoter, may comprise a nematode responsive element isolated from a naturally occurring promoter, or may be a synthetic promoter.

A preferred promoter for use in the present invention is the elongation specific endo-1,4-β-glucanase (cel1) promoter of *Arabidopsis thaliana,* has been described by Z. Shani, M. Dekel, G. Tsabary and O. Shoseyov, *Plant Molecular Biology* 34, 837–842 (1997), and has been assigned EMBL, GenBank and DDBJ Nucleotide Sequence Database accession number X98543. Id. at 837, 839. This promoter is referred to herein as an *Arabidopsis cel*1 promoter, and is set forth herein as SEQ ID NO: 1. The *Arabidopsis cel*1 promoter and other promoters that may be used to carry out the present invention is also disclosed in U.S. Pat. No. 6,005,092 to O. Shoseyov and Z. Shani, issued Dec. 21, 1999, the disclosure of which is incorporated by reference herein in its entirety.

Other DNAs that hybridize to an *Arabidopsis cel*1 promoter under high stringency hybridization conditions as described below, and which encode a nematode responsive promoter (particularly a root knot nematode responsive promoter) may also be used to carry out the present invention.

High stringency hybridization conditions which will permit homologous DNA sequences (e.g., other natural plant DNA sequences) to hybridize to a DNA sequence encoding an *Arabidopsis cel*1 promoter are well known in the art. For example, hybridization of such sequences to a DNA encoding an *Arabidopsis cel*1 promoter may be carried out in 25% formamide, 5×SSC, 5×Denhardt's solution, with 100 μg/ml of single stranded DNA and 5% dextran sulfate at 42° C., with wash conditions of 25% formamide, 5×SSC, 0.1% SDS at 42° C. for 15 minutes, to allow hybridization of sequences of about 60% homology. More stringent conditions are represented by a wash stringency of 0.3M NaCl, 0.03M sodium citrate, 0.1% SDS at 60° or even 70° C. using a standard in situ hybridization assay. (See Sambrook et al., Molecular Cloning, A Laboratory Manual (2d Ed. 1989) (Cold Spring Harbor Laboratory)). In general, plant DNA sequences which code for nematode responsive promoters and which hybridize to the DNA sequence encoding the nematode responsive elements disclosed herein will be at least 75%, 80%, 85%, 90% or even 95% homologous or more with the sequences of the DNA encoding the nematode responsive elements disclosed herein.

It will be apparent that other sequence fragments from the promoter 5' flanking region, longer or shorter sequences, or sequences with minor additions, deletions, or substitutions made thereto, can be prepared which will also encode a nematode responsive promoter, all of which are included within the present invention.

3. Heterologous DNAs and Expression Cassettes

DNA constructs, or "expression cassettes," of the present invention include, 5'-3' in the direction of transcription, a nematode responsive promoter of the present invention, a heterologous DNA segment operatively associated with the promoter, and, optionally, transcriptional and translational termination regions such as a termination signal and a polyadenylation region. All of these regulatory regions should be capable of operating in the transformed cells. The 3' termination region may be derived from the same gene as the transcriptional initiation region or from a different gene.

The term "operatively associated," as used herein, refers to DNA sequences contained within a single DNA molecule which are associated so that the function of one is affected by the other. Thus, a promoter is operatively associated with a gene when it is capable of affecting the expression of that gene (i.e., the gene is under the transcriptional control of the promoter). The promoter is said to be "upstream" from the gene, which is in turn said to be "downstream" from the promoter.

Heterologous DNAs used to carry out the present invention may encode any product that is disruptive of nematode attack when that DNA is transcribed (and, where applicable, translated) in a plant cell, including but not limited to proteins, peptides, and non-protein products such as antisense RNAs, ribozymes, other nucleic acids that suppress expression by sense strand suppression or triplex formation, etc. (see, e.g., U.S. Pat. No. 4,801,540 (Calgene, Inc.)).

The heterologous DNA may encode a product that is toxic to the plant cells, as described in U.S. Pat. No. 5,750,386 to Conkling et al. A wide variety of protein or peptide products which are toxic to plant cells can be used, including (but not limited to) enzymes capable of degrading nucleic acids (DNA, RNA) such as nucleases, restriction endonucleases micrococcal nucleas, Rnase A, and barnase; enzymes which attack proteins such as trypsin, pronase A, carboxypeptidase, endoproteinase Asp-N, endoproteinase Glu-C, and endoproteinase Lys-C; ribonucleases such as RNase CL-3 and RNase T$_1$, toxins from plant pathogenic bacteria such as phaseolotoxin, tabtoxin, and syringotoxin; lipases such as produced from porcine pancrease and *Candida cyclindracea,* membrane channel proteins such as glp F and connexins (gap junction proteins, and antibodies which bind proteins in the cell so that the cell is thereby killed or debilitated. Genes which produce antibodies to plant cell proteins can be produced as described in W. Huse et al., Science 246, 1275–1281 (1989). Proteins to which such antibodies can be directed include, but are not limited to, RNA polymerase, respiratory enzymes, cytochrome oxidase, Krebs cycle enzymes, protein kinases, aminocyclopropane-1-carboxylic acid synthase, and enzymes involved in the shikimic acid pathway such as enolpyruvyl shikimic acid-5-phosphate synthase.

One preferred heterologous DNA is a structural gene encoding mature *Bacillus amyloliquefaciens* RNase (or Barnase). See, e.g., C. Mariani et al., Nature 347, 737–741 (1990); C. Paddon and R. Hartley, Gene 40, 231–39 (1985).

Note that the toxic product may either kill the plant cell in which it is expressed or simply disable the cell so that it is less capable of supporting the pathogen. It is preferred, particularly where the plant is a food plant, that the plant-toxic product be non-toxic to animals, and particularly be non-toxic to humans.

The heterologous DNA may encode any other product disruptive of nematode attack, including but not limited to those described in U.S. Pat. No. 5,589,622 to Gurr et al. (e.g., products toxic to the nematode). Thus the heterologous DNA may encode a *Bacillus thuringiensis* crystal protein toxic to insects. Strains of *B. thuringiensis* which produce polypeptide toxins active against nematodes are disclosed in U.S. Pat. Nos. 4,948,734 and 5,093,120 (Edwards et al.).

Again note that the toxic product may either kill the nematode attempting to feed on the plant cell in which it is expressed or simply disable the nematode so that it is less capable of feeding on the plant cell or establishing a feeding site. For example, the heterologous DNA may encode a peptide, antibody or the like that disrupts feeding by interacting with the ingestion or digestion of food such as one of the antibodies described for soybean cyst nematode including that against the dorsal pharyngeal gland (Atkinson et al, 1988 Annals of Applied Biology 112, 459–469), modified as necessary for specificity to the root knot nematode, using the procedures for transgenic expression of antibodies in plants described by Hiatt, A. Gafferkey, R. C. & Bowdish, K. (1989 Production of Antibodies in Transgenic Plants Nature 342, 76–78).

Again it is preferred, particularly where the plant is a food plant, that the nematode-toxic product be non-toxic to other animals, and particularly be non-toxic to birds, reptiles, amphibians, mammals and humans.

Where the expression product of the gene is to be located in a cellular compartment other than the cytoplasm, the structural gene may be constructed to include regions which code for particular amino acid sequences which result in translocation of the product to a particular site, such as the cell plasma membrane, or secretion into the periplasmic space or into the external environment of the cell. Various secretory leaders, membrane integration sequences, and translocation sequences for directing the peptide expression product to a particular site are described in the literature. See, for example, Cashmore et al., Biotechnology (1985) 3:803–808, Wickner and Lodish, Science (1985) 230:400–407.

The expression cassette may be provided in a DNA construct which also has at least one replication system. For convenience, it is common to have a replication system functional in *Escherichia coli,* such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there may be at least one marker present, which may be useful in one or more hosts, or different markers for individual hosts. That is, one marker may be employed for selection in a prokaryotic host while another marker may be employed for selection in a eukaryotic host, particularly the plant host. The markers may provide protection against a biocide, such as antibiotics, toxins, heavy metals, or the like; may provide complementation by imparting prototrophy to an auxotrophic host; or may provide a visible phenotype through the production of a novel compound in the plant. Exemplary genes which may be employed include neomycin phosphotransferase (NPTII), hygromycin phosphotransferase (HPT), chloramphenicol acetyltransferase (CAT), nitrilase, and the gentamicin resistance gene. For plant host selection, non-limiting examples of suitable markers are beta-glucuronidase (GUS) (providing indigo production), luciferase (providing visible light production), NPTII (providing kanamycin resistance or G418 resistance), HPT (providing hygromycin resistance), and the mutated aroA gene (providing glyphosate resistance).

An advantage of the present invention is that two or more promoters can be "daisychained" to a single structural gene. Where each promoter is responsive to a different pathogen, the plant is then provided with resistance to a plurality of promoters. For example, a second promoter may be positioned upstream from the structural gene and operatively associated therewith so that the structural gene is associated with a plurality of promoters, with each of the promoters activated by a different plant pathogen. Still more promoters can be included if desired. Other promoters that may be used in conjunction with the instant promoter are described in U.S. Pat. No. 5,750,386 to Conkling et al.

The various fragments comprising the various constructs, expression cassettes, markers, and the like may be introduced consecutively by restriction enzyme cleavage of an appropriate replication system and insertion of the particular construct or fragment into the available site. After ligation and cloning, the DNA construct may be isolated for further manipulation. All of these techniques are amply exemplified in the literature. See, e.g., Maniatis et al., Molecular Cloning: A Laboratory Manual, Cold Spring Harbor Laboratory, Cold Spring Harbor, N.Y. (1982).

4. Plant Transformation Vectors and Techniques

A vector is a replicable DNA construct. Vectors which may be used to transform plant tissue with DNA constructs of the present invention include both Agrobacterium vectors and ballistic vectors, as well as vectors suitable for DNA-mediated transformation. *Agrobacterium tumefaciens* cells containing a DNA construct of the present invention, wherein the DNA construct comprises a Ti plasmid, are useful in methods of making transformed plants. Plant cells are infected with an *Agrobacterium tumefaciens* to produce a transformed plant cell, and then a plant is regenerated from the transformed plant cell.

Numerous Agrobacterium vector systems useful in carrying out the present invention are known. For example, U.S. Pat. No. 4,459,355 discloses a method for transforming susceptible plants, including dicots, with an Agrobacterium strain containing the Ti plasmid. The transformation of woody plants with an Agrobacterium vector is disclosed in U.S. Pat. No. 4,795,855. Further, U.S. Pat. No. 4,940,838 to Schilperoort et al. discloses a binary Agrobacterium vector (i.e., one in which the Agrobacterium contains one plasmid having the vir region of a Ti plasmid but no T-DNA region, and a second plasmid having a T-DNA region but no vir region) useful in carrying out the present invention.

Microparticles carrying a DNA construct of the present invention, which microparticle is suitable for the ballistic transformation of a plant cell, are also useful for making transformed plants of the present invention. The microparticle is propelled into a plant cell to produce a transformed plant cell and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050, and in Agracetus European Patent Application Publication No. 0 270 356, titled "Pollen-mediated Plant Transformation". When using ballistic transformation procedures, the expression cassette may be incorporated into a plasmid capable of replicating in the cell to be transformed. Examples of microparticles suitable for use in such systems include 1 to 5 $\mu$m gold spheres. The DNA construct may be deposited on the microparticle by any suitable technique, such as by precipitation.

Plant species may be transformed with the DNA construct of the present invention by the DNA-mediated transformation of plant cell protoplasts and subsequent regeneration of the plant from the transformed protoplasts in accordance with procedures well known in the art.

5. Plants for Transformation and Propagation of Transformants

Plants that may be used to carry out the present invention are typically vascular plants (including angiosperms and gymnosperms, monocots and dicots).

Cells used to carry out the present invention may be vascular plant cells, which may reside in vitro or in vivo in a plant tissue or intact plant, but other cell types such as bacterial cell may be employed to carry out intervening steps involved in preparing the DNA constructs employed in carrying out the present invention.

A transformed plant or host cell is a plant or host cell which has been transformed or transfected with DNA constructs as disclosed herein, using recombinant DNA techniques such as those described above coupled with propagation techniques such as those described below.

The promoter sequences disclosed herein may be used to express a heterologous DNA sequence in any plant species capable of utilizing the promoter (i.e., any plant species the RNA polymerase of which binds to the promoter sequences disclosed herein). Examples of plant species suitable for transformation with the DNA constructs of the present invention include both monocots and dicots, and include but are not limited to tobacco, soybean, potato, cotton, sugarbeet, sunflower, carrot, celery, flax, cabbage and other cruciferous plants, pepper, tomato, citrus trees, bean, strawberry, lettuce, maize, alfalfa, oat, wheat, rice, barley, sorghum and canola. Thus an illustrative category of plants which may be transformed with the DNA constructs of the present invention are the dicots, and a more particular category of plants which may be transformed using the DNA constructs of the present invention are members of the family Solanacae.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

6. Uses of the Invention

The present invention may be used in the manner described in U.S. Pat. No. 5,750,386 to Conkling et al. or U.S. Pat. No. 5,589,622 to Gurr et al. Thus, the present invention provides a method of controlling nematodes, comprising: (a) providing a root knot nematode-responsive promoter as described above, (b) preparing a construct as described above by combining said promoter with a further region which codes for a product disruptive of nematode attack, and (c) transforming plants with the construct to obtain plants which are root knot nematode resistant. The plants employed may be as described above, and transformation may be carried out as described above. Once a first generation ($F_O$ generation) of transformed plants are obtained, plant seed that contains the aforesaid construct, and that germinates into a root knot nematode resistant transgenic plant, may be be produced from the $F_O$ plants by conventional breeding procedures. An agricultural field infected with root knot nematodes, or susceptible to root knot nematode infection, can then be planted with a crop of such plants in accordance with standard techniques (e.g., by planting seed or plantlets) to provide an agricultural field of crop plants that are resistant to root knot nematode infection.

The present invention is explained in greater detail in the following non-limiting Examples.

EXAMPLE 1

Tobacco seed containing the *Arabidopsis cel*1 promoter fused to and driving a GUS gene, previously described in Z. Shani et al., *Plant Molec. Biol.* 34, 837–842 (1997), were provided by Dr. Oded Shoseyov.

Plants were grown from the seed and infected with the tobacco cyst nematode. The *cel*1-GUS transgenic tobacco roots did not exhibit GUS staining other than in the elongation zone of the root tips. However, it was also found that plants infected with the root knot nematode (*Meloidogyne incognita*), which also parasitizes tobacco, specifically upregulated *cel*1-GUS in specialized feeding sites called giant cells around which galls form on the roots. See FIG. 1. A time course study was carried out from the time of infection through the root knot nematode life cycle, and it was found that expression correlates with the onset of giant cell formation and is maintained throughout the nematode life cycle (up to about 2 months). Roots were sectioned and it was found that GUS staining was specifically localized in the giant cells.

The foregoing is illustrative of the present invention, and is not to be construed as limiting thereof. The invention is defined by the following claims, with equivalents of the claims to be included therein.

That which is claimed is:

1. A transformed plant comprising transformed plant cells, said transformed plant cells containing a DNA construct which comprises, in the 5' to 3' direction:
   (a) DNA encoding the root knot nematode-responsive promoter of SEQ ID NO:1; and
   (b) a heterologous DNA positioned downstream from said promoter and operatively associated therewith, said heterologous DNA encoding Barnase.

2. The transformed plant according to claim 1, wherein said plant is a dicot.

3. The transformed plant according to claim 1, wherein said plant is a monocot.

4. The transformed plant according to claim 1, wherein said plant is a tobacco (*Nicotirina tabaaim*) plant.

5. A Plant seed that germinates into the plant of claim 1.

6. A method of controlling root knot nematodes, comprising the steps of:
   (a) providing a root knot nematode-responsive promoter of SEQ ID NO:1
   (b) preparing a construct by combining said promoter with a further heterologous region which codes for a product disruptive of nematode attack, and
   (c) transforming plants with the construct to obtain plants which are root knot nematode resistant.

7. The method according to claim 6, wherein said plants are monocots.

8. The method according to claim 6, wherein said plants are dicots.

* * * * *